United States Patent [19]

Cray et al.

[11] Patent Number: 4,978,561
[45] Date of Patent: Dec. 18, 1990

[54] TREATMENT OF FIBROUS MATERIALS

[75] Inventors: Stephen E. Cray; James McVie, both of South Glamorgan, Wales; Paul A. Yianni, Limal, Belgium

[73] Assignee: Dow Corning Limited, Barry, Wales

[21] Appl. No.: 353,313

[22] Filed: May 17, 1989

[30] Foreign Application Priority Data

May 17, 1988 [GB] United Kingdom ............... 8811602
Feb. 9, 1989 [GB] United Kingdom ............... 8902938

[51] Int. Cl.$^5$ ............................................. B05D 3/02
[52] U.S. Cl. ................................. 427/387; 252/8.8; 427/392; 428/447; 428/452; 528/26; 528/38
[58] Field of Search ............ 427/387, 389.9, 392; 528/26, 38; 252/8.8; 428/447, 452

[56] References Cited

U.S. PATENT DOCUMENTS 4,591,652 5/1986 DePasquale et al. ............... 556/419
4,624,794 11/1986 Cooke et al. ........................ 252/8.8
4,749,732 6/1988 Kohl et al. .......................... 524/43

*Primary Examiner*—Michael Lusignan
*Attorney, Agent, or Firm*—George A. Grindahl

[57] ABSTRACT

The specification describes and claims a method of treating fibrous material which comprises applying to the fibrous material a composition comprising an organosilicon compound having a group =NCO(CH$_2$)$_n$OH connected with a silicon atom of the organosilicon compound. The organosilicon compound consists of or comprises (A) a silane according to the genral formula $R^1_a A_b Si(R''NXR')_c$ or (B) a polysiloxane comprising one or more siloxane units according to the general formula (i)

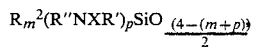

any remaining units of the polysiloxane being at least predominantly according to the general formula (ii)

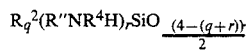

A represents a hydroxyl or a hydrolysable group, $R^1$ represents a monovalent hydrocarbon group having up to 8 carbon atoms, $R^2$ represents a hydroxyl group, a group $R^1$, a group $OR^1$ or a group $COR^1$, $R^4$ represents a hydrogen atom, an alkyl group having 1 to 20 carbon atoms, an alkenyl group or an aryl group, $R^1$ represents a group $R^4$ or a group X, R" represents a divalent hydrocarbon group which may have nitrogen, oxygen or sulphur present in the carbon chain, X represents a group $CO(CHR)_n OH$ in which R represents a hydrogen atom, a hydroxyl group, a hydrocarbon group or a hydroxyl substituted hydrocarbon group a has the value 0, 1 or 2, b has the value 1, 2 or 3, c has the value 1 or 2, the sum of a+b+c=4, m has the value 0, 1 or 2, p has the value 1 or 2, q has the value 0, 1, 2 or 3, r has the vale 0, 1 or 2 and n has a value in the range 2 to 7. Fabrics treated according to the method have a satisfactory handle and improved non-yellowing properties.

23 Claims, No Drawings

TREATMENT OF FIBROUS MATERIALS

This invention is concerned with treatment of fibrous materials.

By the expression "fibrous material" where used herein is meant strands, filaments and the like of synthetic polymeric materials or animal or vegetable materials including, for example, keratinous materials (for example human hair), wool and cotton. The present invention is applicable to the treatment of fibrous materials both in treatment of the fibres and in treatment of textiles incorporating the fibres, the treatment being applicable on the fibres at the time of production of a textile fabric, or at the time of laundering the textile fabric.

It is known to treat fibrous materials with polysiloxanes to impart desirable properties thereto. For example it is known to treat textile fabrics with polysiloxanes to impart water repellency, lubricity and crease resistance. Proposals have been made to treat textile fabrics with aqueous emulsions or dispersions comprising amino substituted polysiloxanes and this has led to provision of compositions capable of conferring extremely soft handle to textile fabrics. Unfortunately, however, available amino substituted polysiloxane based compositions tend to impart a yellow colouring to the fabric which is regarded as a disadvantage in some respects. It is desirable to provide a method of treating fibrous materials which yields materials having an acceptable level of softness and yet which does not impart or develop a yellow colouring. It has been proposed to prepare amide containing polysiloxanes by reaction of an amine substituted polysiloxane with an acid anhydride, for example, acetic anhydride. These amide containing polysiloxanes have the advantage that they can be formulated into non-yellowing fabric finishes. However, a by-product of the reaction is the free acid, which may interfere with emulsification of the polysiloxane and which, in a fabric finish, is undesirable with respect to handling of the product in view of for example corrosive properties of the composition. Additionally, fabric finishes based on these amide containing polysiloxanes, when used to treat fabrics, tend to yield treated fabrics having a degree of harshness.

We have now found that fibrous materials treated with amino substituted polysiloxanes which have been modified at least partially by reaction with a lactone demonstrate a good level of softness, and a more acceptable degree of yellowing.

The present invention provides in one of its aspects a method of treating fibrous material which comprises applying to the fibrous material a composition comprising a polydiorganosiloxane having a group =NCO(CHR)$_n$OH connected with a silicon atom of a siloxane unit of the polydiorganosiloxane wherein R represents a hydrogen atom, a hydroxyl group, or a hydrocarbon group or a hydroxyl substituted hydrocarbon group and n has a value in the range 2 to 7.

Organosilicon compounds for use in a method of the present invention may be prepared by reaction between a lactone and a silicon compound having an amino substituent. Suitable lactones have the formula

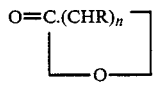

which R represents a hydrogen atom, a hydroxyl group, a hydrocarbon group e.g. an alkyl group having for example, up to 7 carbon atoms, or a hydroxyl substituted hydrocarbon group having for example up to 7 carbon atoms, such as may be present when the lactone has been derived from a γ hydroxy acid. Preferred lactones are those in which each R represents a hydrogen atom, a hydroxyl group or a hydroxy alkyl group and n has the value 3, 4, 5 or 6, for example γ butyrolactone and epsilon caprolactone in which all the R's are hydrogen atoms, and delta gluconolactone which is to say the lactone in which three R groups are hydroxyl groups and one is the group $CH_2OH$ and the remainder are hydrogen atoms and n is 5. Most preferred lactones are those in which each R represents a hydrogen atom and n has the value 3, 4, 5 or 6, for example γ butyrolactone and epsilon caprolactone. Reaction of the delta gluconolactone proceeds with greater difficulty than that of the caprolactone and the butyrolactone and tends to yield more viscous polymers which are less easy to manipulate. Thus, we prefer to employ butyrolactone.

Various amino substituted organosilicon compounds are known and available, and they can be made by methods known in the art. The amino substituted organosilicon compound may be (A) a silane according to the general formula $R^1{}_aA_bSi(R\Delta NR^4H)_c$ or (B) a polysiloxane having one or more siloxane units according to the general formula (iii)

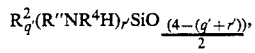

any remaining units of the polysiloxane being according to the general formula (iv)

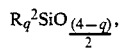

wherein A represents a hydroxyl group or a hydrolysable group, $R^1$ represents a monovalent hydrocarbon group having up to 8 carbon atoms, $R^2$ represents a hydroxyl group, a group $R^1$, a group $OR^1$ or a group $COR^1$, $R^4$ represents a hydrogen atom, an alkyl group having 1 to 20 carbon atoms, an alkenyl group or an aryl group, R" represents a divalent hydrocarbon group which may have nitrogen, oxygen or sulphur present in the carbon chain, a has the value 0, 1 or 2, b has the value 1, 2 or 3, c has the value 1 or 2, the sum of $a+b+c=4$, q has the value 0, 1, 2, or 3, q' has the value 0, 1 or 2, and r' has the value 1 or 2. The aminosilane (A) may have hydrolysable groups selected from, for example, alkoxy, alkoxyalkoxy, acetoxy and chloro. The amino substituted polysiloxanes may be prepared from precursors comprising one or more hydroxy polysiloxanes and hydrolysable aminosilanes. The alkoxy silanes are generally preferred. Suitable hydroxy polysiloxanes include those in which the organo groups are at least predominantly alkyl groups having up to eight carbon atoms. When preparing an amino substituted polysiloxane intended for use in preparation of organosilicon compounds according to the invention, if desired, a silicone material capable of providing a desired degree of chain branching in the polysiloxane may be employed among the precursors for the amino substituted polysiloxane. Suitable materials are silanes $R^1A_3Si$ and $A_4Si$. The amino substituted polysiloxane may be condensed and or equilibrated with selected organosilicon compounds of appropriate structure and molecular weight. Desirably the amino substituted polysiloxane has a major proportion of siloxane units of the general formula

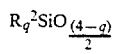

$$R_q^2 SiO_{\frac{(4-q)}{2}}$$

and a minor proportion of siloxane units of the general formula

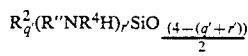

$$R_{q'}^2(R''NR^4H)_{r'}SiO_{\frac{(4-(q'+r'))}{2}}$$

wherein $R^2$, $R''$, $R^4$, $q'$ and $r'$ are as aforesaid. Preferred materials are those wherein $R''$ represents $R'''(NR'R''')_s$ wherein $R'''$ represents a divalent hydrocarbon group, $R'$ is a group $R^4$ and s has a value in the range 0 to 4, more preferably 1 or 2. Examples of suitable groups $R'''$ include —$(CH_2)_2$—, —$(CH_2)_3$—, —$(CH_2)_4$— and —$CH_2CH(CH_3)CH_2$—. Operative amino containing substituents $R''NR^4H$ include —$(CH_2)_3NH_2$, —$(CH_2)_3NHCH_2CH_2NH_2$, —$CH_2CH(CH_3)CH_2NHCH_2CH_2NH_2$, and —$(CH_2)_3$—$NHCH_2CH_2NHCH_2CH_2NH_2$. Preferred amino substituted polysiloxanes are those in which the $R^2$ groups are lower alkyl e.g. methyl groups or phenyl groups, and which have two or more amino siloxane units per molecule. Most preferred are those in which at least 80% of the groups $R^2$ are methyl groups.

The organosilicon compounds for use in the invention may be made by any convenient method, for example, by modification of some or all of the amino groups of the appropriate aminopolysiloxane or by modification of the appropriate aminosilane. The silane produced may be hydrolysed to provide a polysiloxane, or condensed with a siloxane or other silane in known manner to provide a polysiloxane. Polysiloxanes produced may be condensed with a silane or siloxane in known manner to provide further polysiloxanes. If desired the condensation step may be followed by equilibration and separation in known manner. Reaction between the lactone and the amino substituted organosilicon compound to form the amide containing organosilicon compound may be carried out under a variety of conditions and is preferably carried out by heating the reactants together, optionally, for example in aqueous emulsion or in solution, most preferably under reflux in, for example methyl ethyl ketone, toluene or ethanol. The proportions of the reactants employed may be chosen so that the desired proportion of the amino groups of the amino substituted organosilicon compound are converted to the amido form. For example one may ensure that from 20 to 80% of the primary amino groups are modified by reaction with the lactone.

The invention provides in one of its aspects a method of treating fibrous material which comprises applying to the fibrous material a composition comprising a polysiloxane having one or- more siloxane units according to the general formula (i(

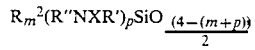

$$R_m^2(R''NXR')_p SiO_{\frac{(4-(m+p))}{2}}$$

any remaining units of the polysiloxane being at least predominantly according to the general formula (ii)

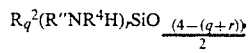

$$R_q^2(R''NR^4H)_r SiO_{\frac{(4-(q+r))}{2}}$$

wherein $R^2$ represents a hydroxyl group, a group $R^1$, a group $OR^1$ or a group $COR^1$, $R^1$ represents a monovalent hydrocarbon group having up to 8 carbon atoms, $R^4$ represents a hydrogen atom, an alkyl group having 1 to 20 carbon atoms, an alkenyl group or an aryl group, $R'$ represents a group $R^4$ or a group X, $R''$ represents a divalent hydrocarbon group which may have a nitrogen, oxygen or sulphur atom present in the carbon chain, X represents a group $CO(CHR)_nOH$ in which R represents a hydrogen atom, a hydroxyl group, a hydrocarbon group or a hydroxyl substituted hydrocarbon group, m has the value 0, 1 or 2, p has the value 1 or 2, q has the value 0, 1, 2 or 3, r has the value 0, 1 or 2 and n has a value in the range 2 to 7.

The invention provides in another of its aspects a method of treating fibrous material which comprises applying to the fibrous material a composition comprising a silane or a polysiloxane formed by hydrolysis or condensation of a silane, the silane being according to the general formula $R^1_aA_bSi(R''NXR')_{c1}$ wherein A represents a hydroxyl or hydrolysable group, $R^1$ represents a monovalent hydrocarbon group having up to 8 carbon atoms, $R'$ represents a hydrogen atom, an alkyl group having 1 to 20 carbon atoms, an alkenyl group, an aryl group or a group X, $R''$ represents a divalent hydrocarbon group which may have a nitrogen, oxygen or sulphur atom present in the carbon chain, X represents a group $CO(CHR)_nOH$ in which R represents a hydrogen atom, a hydroxyl group, a hydrocarbon group or a hydroxyl substituted hydrocarbon group a has the value 0, 1 or 2, b has the value 1, 2 or 3, c has the value 1 or 2, the sum of $a+b+c=4$ and n has a value in the range 2 to 7.

The hydrolysable groups A of the silane (A) may be selected, for example from alkoxy, (e.g. methoxy, ethoxy or propoxy) alkoxyalkoxy (e.g. methoxy-ethoxy) acetoxy and halogen (e.g. chlorine). The silanes (A) are hydrolysable materials and may be employed as such in the preparation of a composition for use in the invention, or may be incorporated into a polysiloxane for use in preparation of a composition for use in the invention, as end blocking, chain extending or chain branching units of the polysiloxane depending on the values of a and b. They may be hydrolysed to provide a polysiloxane with or without the presence of other silanes, for example to provide a polysiloxane (B), or condensed with, for example polysiloxanes having hydroxyl or other reactive groups, for example linear $\alpha,\omega$ dihydroxypolysiloxanes, to provide a polysiloxane (B). The polysiloxanes (B) comprise at least one, and preferably two or more, units according to the general formula (i). The polydiorganosiloxane (B) also contains siloxane units according to the general formula (ii)

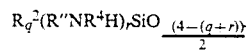

$$R_q^2(R''NR^4H)_r SiO_{\frac{(4-(q+r))}{2}}$$

R" in this formula may represent R''' (N'R''') as referred to above. Preferred polysiloxanes for use in the invention include both siloxane units (ii) which have groups R"NR⁴H and siloxane units (ii) which have no groups R"NR⁴H. Preferred polysiloxanes have 90% or more, suitably more than 95% and preferably 97 to 99% of siloxane units (ii) according to the general formula

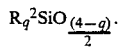

If desired, the polysiloxane may also comprise one or more siloxane units having other substituent groups, for example oxyalkylene glycol groups. The groups $R^1$ are preferably alkyl groups, the methyl group being the most preferred. Preferred groups R"NXR' are according to the general formula

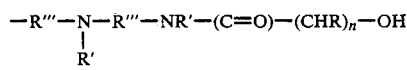

in which R''' is selected from the groups —(CH$_2$)$_2$—, —(CH$_2$)$_3$—, —(CH$_2$)$_4$— and —CH$_2$CH(CH$_3$)CH$_2$— and R' represents a hydrogen atom. Preferred polysiloxanes are at least substantially linear materials, the most preferred being according to the average general formula

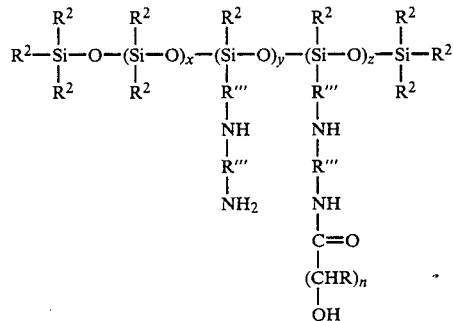

Preferred materials are those in which not less than 80% of the groups $R^2$ are methyl groups, x has a value from 20 to 1500, y may be 0 or may have an average value greater than 0, for example in the range 0.5 to 10, and z has an average value greater than 0, for example in the range 0.5 to 10, the ratio of y:z (when y is greater than 0) lies in the range 1:4 to 4:1 and the ratio z:x is less than 5 : 100.

Preferred organosilicon compounds for use in a method of the invention are thus materials in which the group =NCO(CHR)$_n$OH is part of a substituent linked to the silicon atom which substituent is selected from —R'''NXR' and —R'''NR'R'''NXR', wherein R''' is as aforesaid, R' represents a hydrogen atom, a group X, a group R'''NXR', an alkyl group having 1 to 20 carbon atoms, an alkenyl group or an aryl group and X represents a group —CO(CHR)$_n$OH wherein n has a value in the range 2 to 7. The preferred polysiloxanes comprise principally units of formula (ii)

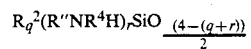

in which r has the value 0, at least one unit and preferably two or more units of the formula (i)

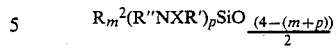

wherein $R^2$, X, m and p are as aforesaid, and one or more units of the formula (ii) in which r has the value 1 or 2.

Preferred materials for preparing polysiloxanes which are intended for application in the form of an aqueous emulsion to fibres and fabrics are substantially linear materials. They may have a viscosity in excess of 50,000 but we prefer to employ materials having viscosities of less than 50,000 mm$^2$/s, more preferably less than 5000 mm$^2$/s.

The composition employed in a method according to the invention may be in any suitable form e.g. solution, dispersion or emulsion. The preferred polysiloxanes may be provided in aqueous form as dispersions or emulsions (e.g. by emulsion polymerisation or mechanical emulsification) and the most preferred are capable of provision as clear microemulsions according to European patent specification No. 138 192. The aqueous forms are particularly desirable and may be formulated so as to become cured on the substrate to which they have been applied. The composition may comprise curatives' polydimethyl siloxanes, biocides and/or other ingredients commonly employed in compositions for treating fibrous materials. The method of the invention is suitable for treatment of natural fibres, for example human hair or freshly laundered textile fabrics incorporating fibres of cotton, which may be blended with other fibres for example polyester, to provide a finish which confers a good handle or feeling of softness, and a less yellow colouring to the fabric than similar treatments with the corresponding amino polysiloxane which has not been treated with the lactone. Those organosilicon compounds having both amido siloxane units as specified and primary amino substituted siloxane units may be used for the treatment of fibres and particularly natural fibres, for example textile fabrics incorporating fibres of cotton, to provide a finish which shows a desirable blend of softness, whiteness and durability at least through several washings. The preparation of organosilicon compounds of the invention from the appropriate lactone and silicon compound is particularly beneficial as no undesirable by product is released during the reaction.

In order that the invention may become more clear there now follows a description of example compositions and examples of their use for treating fibrous materials which methods are illustrative of the invention.

In the Examples all parts and percentages are expressed by weight unless otherwise specified and Me signifies the methyl group.

EXAMPLE 1

253.7 parts (0.037 moles) of a polysiloxane of the average general formula

Me$_3$SiO(Me$_2$SiO)$_{195.5}$(MeQSiO)$_{4.5}$SiMe$_3$ in which Q represents the group CH$_2$.CHMe.CH$_2$ NH.(CH$_2$)$_2$NH$_2$ (aminosiloxane 1), 7 parts (0.0814 moles) Y butyrolactone

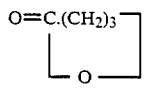

and 100 parts of toluene were heated at 80° C. for 5 hours under nitrogen, with constant stirring and reflux. The product was stripped of toluene using a rotary evaporator. The polysiloxane produced (Example polysiloxane 1) was a slightly yellow fluid having a viscosity of 2920 mm:/s at 25° C. Spectroscopic studies (NMR) showed the polymer contained amido groups and analysis of the nitrogen content of the polymer by acid titration showed that all primary amino groups of the polysiloxane had been converted. It was thus determined that Example polysiloxane 1 was of the formula $Me_3SiO(Me_2SiO)_{195.5}(MeQ'SiO)_{4.5}SiMe_3$
in which Q' represents the group $CH_2CHMeCH_2NH(CH_2)_2NHCO(CH_2)_3OH$.

EXAMPLE 2

172.7 parts (0.0222 moles) of aminosiloxane 1, 5.73 parts (0.0503 moles) epsilon caprolactone

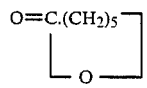

and 100 parts toluene were heated at 80° C. for 5 hours under nitrogen, with constant stirring and reflux. The product was stripped of toluene using a rotary evaporator. The polysiloxane produced (Example polysiloxane 2) was a slightly yellow fluid having a viscosity of 11,100 mm$^2$/s at 25° C. From spectroscopic studies (NMR) and analysis of the nitrogen content of the polymer it was determined that Example polysiloxane 2 was of the formula $Me_3SiO(Me_2SiO)_{195.5}(MeQ''SiO)_{4.5}SiMe_3$
in which Q'' represents the group $CH_2CHMeCH_2NH(CH_2)_2NHCO(CH_2)_5OH$.

EXAMPLE 3

489.3 parts (0.0630 moles) of a polysiloxane of the average general formula $Me_3SiO(Me_2SiO)_{98}(MeQSiO)_2SiMe_3$
in which Q represents the group $CH_2.CHMe.CH_2.NH.(CH_2)_2NH_2$ (aminosiloxane 2), and 13.1 parts (0.152 moles) Y butyrolactone were heated at 80° C. for 5 hours under nitrogen, with constant stirring and reflux. The polysiloxane produced (Example polysiloxane 3) had a viscosity of 922 mm$^2$/s at 25° C. From spectroscopic studies (NMR) and analysis, it was determined that Example polysiloxane 3 was of the formula $Me_3SiO(Me_2SiO)_{98}(MeQ'SiO)_2SiMe_3$
in which Q' represents the group $CH_2.CHMe.CH_2.NH.(CH_2)_2NHCO(CH_2)_3OH$.

EXAMPLE 4

100 parts of aminosiloxane 1, 11.7 parts delta gluconolactone, 400 parts methyl ethyl ketone and 1 part ammonium acetate were heated at 80° C. for 13 hours under nitrogen, with constant stirring and reflux.

The polysiloxane product was decanted from the remaining lactone and the solvent stripped from the product. Spectroscopic studies (NMR) and analysis of nitrogen content showed the polymer to be of the formula $Me_3SiO(Me_2SiO)_{195.5}(MeQ'SiO)_{4.5}SiMe_3$
in which Q' represents the group $CH_2.CHMe.CH_2.NH.(CH_2)_2NHCO(CHOH\ CH_2OH)$.

EXAMPLE 5

45.6 parts of a trimethylsilyl end-blocked polydimethylsiloxane, 1387.1 parts dimethyl cyclic siloxanes, 71.1 parts $(MeQSiO)_4$ wherein Q represents $CH_2CH(Me)CH_2NH(CH_2)_2NH_2$ and 9.2 parts potassium silanolate were heated at 150° C. under nitrogen for 5 hours. The product was then allowed to cool to 70° C. and 0.48 part glacial acetic acid was added to the product which was then stirred for a further hour at 70° C. It was then allowed to cool to room temperature and then filtered. The resulting clear colourless fluid had a viscosity of 150mm$^2$/s. 1080.6 parts of this fluid and 28.7 parts of Y butyrolactone were heated at 80° C. under nitrogen for 5 hours. The resulting Example polysiloxane 4 was a clear, slightly yellow, fluid having a viscosity of 1472 mm$^2$/s and was of the average general formula $Me_3SiO(Me_2SiO)_{98}(MeQ'SiO)_2SiMe_3$
in which Q' represents the group $CH_2CHMeCH_2NH(CH_2)_2NHCO(CH_2)_3OH$

EXAMPLE 6

The amide containing polysiloxane of Example 4 and each of the Example polysiloxanes 1, 2, 3 and 5 was found capable of formulation as a solution or emulsion which when applied to a cotton fabric exhibited acceptable non-yellowing characteristics and conferred a soft handle to the fabric.

The performance of Example polysiloxane 3 as a fabric treating material was compared with that of an amino substituted polysiloxane based fabric finish in the following way. 15 parts of Example polysiloxane 3 were mixed with 9 parts of a non-ionic, ethoxy based surfactant, 0.25 part glacial acetic acid and 75.7 parts water and mixed to produce a first microemulsion. A second microemulsion was made up using 15 parts of an amino functional polysiloxane (C) according to the average general formula $Me_3SiO(Me_2SiO)_{392}(MeQ'SiO)_8SiMe_3$
in which Q represents the group $CH_2.CHMe.CH_2.NH.(CH_2)_2NH_2$, 9 parts of non-ionic, ethoxy based surfactant, 0.3 part glacial acetic acid, 0.2 part biocide and 75.5 parts water.

The microemulsions were used to provide first and second pad baths respectively, which were applied by padding to samples of woven cotton textile fabric. The cotton fabric as received had been treated with an optical brightening agent. The polysiloxanes were used in the padding baths in a concentration to provide 0.7% of the polysiloxane on the weight of the fabric. After removal from the pad bath the samples were heated for 2 minutes at 110° C. and then for 45 seconds at 170° C. The samples were aged for 24 hours and then assessed for whiteness and softness. Whiteness was judged by the human eye and by a Hunterlab tristimulus colorimeter system. In the accompanying Table I, the higher numbers indicate greater whiteness; a difference of 2 or more is visible to the human eye and the results from the colorimeter were comparable with those from the human eye. Softness was evaluated by a panel of handle assesors on a scale of 0 to 10, with 0 being the softest: the average result is recorded in the Table.

TABLE I

|  | Whiteness | Softness |
|---|---|---|
| Sample from pad bath containing no polysiloxane | 111.3 | 0 |
| Sample from pad bath containing Example polysiloxane 3 | 107.3 | 10 |
| Sample from pad bath containing polysiloxane C | 105.6 | 9 |

From the Table it can be seen that the sample treated with the Example polysiloxane 3 was whiter and softer than that treated with the polysiloxane C.

EXAMPLE 7

Silanes 1, 2, and 3 were made as follows. Silane 1 was prepared thus: 1.63 moles of the silane $Me.(MeO)_2SiQ$ in which Q represents the group $CH_2.CHMe.CH_2.NH.(CH_2)_2NH_2$ were charged to a split-necked flask fitted with reflux condenser, stirrer and thermometer. 1.63 moles γ butyrolaotone

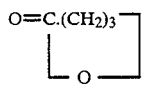

were added dropwise to the silane in the flask and the mixture stirred and heated to 80° C. The reacting mixture was maintained at this temperature under a blanket of nitrogen for five hours. The mixture was allowed to cool in the flask. The product (Silane 1) was a viscous yellow liquid having a viscosity at 25° C. of 129,600 mm²/s of the formula

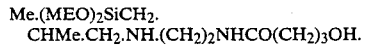

Silane 2 was prepared in the same manner as Silane 1 except that the group Q of the aminosilane employed was $(CH_2)_3.NH.(CH_2)_2NH_2$. Silane 2 had a viscosity of 38,000 mm²/s at 25° C. Silane 3 was prepared in similar fashion to Silane 1 except that the silane $(MeO)_3SiQ$ in which Q represents the group $CH_2.CHMe.CH_2.NH.(CH_2)_2NH_2$ was used as starting material. Silane 3 was a viscous yellow liquid having a viscosity of 43,280 mm²/s at 25° C.

2 moles of Silane 1 was mixed with 1 mole of α,ω dihydroxypolydimethyl siloxanes having a viscosity of 150 mm²/s, heated to 50° C. for four hours and then cooled to room temperature. An aqueous emulsion was prepared using this product together with an ethoxy based surfactant. The emulsion was padded onto a cotton fabric such that about 0.7% silicone solids was present on the weight of the fabric. The fabric was found to exhibit non-yellowing characteristics and to confer a soft handle to the fabric.

EXAMPLE 8

Example polysiloxanes 5, 6 and 7 were prepared according to the method described in Example 5, except that the aminosiloxane and lactone were employed in proportions to convert 25%, 50% and 75% respectively of the primary amino groups present to amido groups $=NCO(CHR)_nOH$.

These polysiloxanes 5, 6 and 7 were according to the average general formula

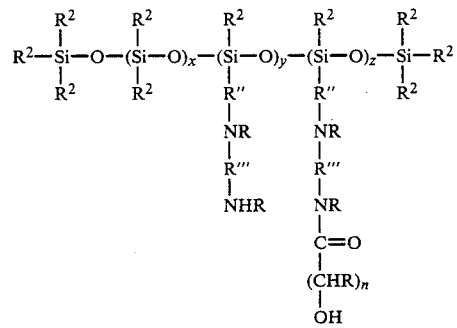

in which each $R^2$ represents a methyl group, each R represents a hydrogen atom, each R" represents $—CH_2CH(CH_3)CH_2—$, each R''' represents $—CH_2.CH_2—$ and n is 3, the siloxane units being in proportions such that the values of x, y and z were as shown in Table II.

TABLE II

| Polysiloxane | x | y | z | Ratio y:z |
|---|---|---|---|---|
| 5 | 98 | 1.5 | 0.5 | 3:1 |
| 6 | 98 | 1 | 1 | 1:1 |
| 7 | 98 | 0.5 | 1.5 | 1:3 |

EXAMPLE 9

Microemulsions were produced and their performance on woven cotton fabric was examined. The microemulsions were made up as described in Example 6 using polysiloxane C, aminosiloxane 1 and Example polysiloxanes 3, 4, 5, 6 and 7. The emulsions were padded onto woven cotton fabric and the softness of the fabric samples evaluated as described in Example 6. Softness of the samples was evaluated before and after five wash cycles and the durability of the treatment thus assessed. For this purpose, the samples were washed and dried according to International Standard 6330 using washing procedures for horizontal drum machines type A1, Procedure No 6A and a tumble drier using 2kg of samples and Persil washing powder. The results are shown in Table III.

TABLE III

| | | Softness | |
|---|---|---|---|
| Poly-siloxane | y/z | before washing | after washing (5 cycles) |
| None | — | 0 | |
| C | — | 10 | 8 |
| 3 | | 10 | 4 |
| 4 | | 10 | 4 |
| 5 | 3 | 10 | 8 |
| 6 | 1 | 10 | 8 |
| 7 | 0.33 | 10 | 6 |
| amino-siloxane 1 | | 10 | 8 |

As can be seen from Table III, whereas all the fabric samples showed a comparable level of softness prior to washing, the samples treated with polysiloxane having at least some primary amino siloxane units showed a better retention of their softness, samples treated with those polysiloxanes having a ratio y:z of 1:1 or 3:1 being the best in this respect.

EXAMPLE 10

Microemulsions were produced and their performance on woven cotton fabric was examined. The microemulsions were made up as described in Example 6 using Example polysiloxanes 3, 5, 6 and 7, aminosiloxane 2 and an amidopolysiloxane D according to the general formula $$Me_3SiO(Me_2SiO)_{98}(MeSiBO)_2SiMe_3$$

wherein B represents $CH_2CHMe.CH_2NHCH_2CH_2NHCOCH_3$ obtained by reaction of a portion of aminosiloxane 1 and sufficient acetic anhydride to convert all the primary amino groups of the aminosiloxane to amide groups.

The emulsions were padded onto woven cotton fabric to provide 1% by weight silicone solids on the fabric, and onto polyester cotton fabric (65/35) to provide 0.5% by weight silicone solids on the fabric. The treated cotton fabric samples were dried at 110° C. for 2 minutes and cured at 150° C. for 2 minutes. The polyester cotton fabric samples were dried at 110° C. for 1 minute and cured at 180° C. for 30 seconds. Softness of the samples was evaluated as described in Example 5 and the whiteness index of each sample was measured using the Hunterlab colorimeter system. The results for woven cotton samples are shown in Table IV and those for polyester cotton samples are shown in Table V.

TABLE IV

| Polysiloxane | Whiteness | Softness |
|---|---|---|
| None | 50.5 | 0 |
| Aminosiloxane 2 | 40.0 | 8.8 |
| Example 5 | 42.4 | 8.0 |
| Example 6 | 43.7 | 7.0 |
| Example 7 | 42.7 | 6.6 |
| Example 3 | 47.4 | 6.6 |
| Amidosiloxane D | 49.2 | 2.8 |

TABLE V

| Polysiloxane | Whiteness | Softness |
|---|---|---|
| None | 75.7 | 0.4 |
| Aminosiloxane 2 | 69.6 | 8.2 |
| Example 5 | 68.2 | 6.8 |
| Example 6 | 69.4 | 7.6 |
| Example 7 | 71.3 | 8.8 |
| Example 3 | 74.0 | 7.6 |
| Amidosiloxane D | 77.5 | 4.0 |

As can be seen from Tables IV and V the samples of cotton fabric treated with those polysiloxanes having at least some amidosiloxane units formed from reaction with a lactone as hereinbefore described (Example polysiloxanes 3, 5, 6 and 7) showed greater whiteness than samples treated with aminosiloxane 2 containing no such groups. The polyester-cotton samples indicate that not less than 50% of the primary amino groups should be converted via the lactone reaction to enable provision of fabrics having desirable whiteness and softness. Samples of both types of fabrics treated with the polysiloxanes having lactone modified amino groups showed a much more acceptable softness compared with samples made using amidosiloxane D.

EXAMPLE 11

This Example shows the conditioning effect on human hair of the microemulsion used in Example 6 formed with Example polysiloxane 3. The performance of the microemulsion was compared with that of an aqueous cationic emulsion of pH about 7.6 containing 0.35% of polydimethylsiloxanes having amine functionality and hydroxyl functionality according to the average general formula $$HO(Me_2SiO)_x(OHR'SiO)_ySiMe_2OH$$

in which the ratio x/y is approximately 100 and R' represents $-(CH_2)_3NH(CH_2)_2NH_2$, in admixture with cationic surfactants. Swatches of human hair were dipped in compositions prepared from the microemulsion and the cationic emulsion containing 0.75% polysiloxane. Evaluation by combing the hair, both when wet and when dry and by assessing the static in the hair showed the performance of the Example polysiloxane 3 to be comparable with that of the cationic emulsion, in that both gave good combing properties, and the dried swatches had a soft bouncy character. Similar results were observed when the polysiloxanes were employed in a hair shampoo in which hair swatches were washed and which comprised 0.75 part of the appropriate polysiloxane, 20 parts sodium lauryl sulphate, 3.5 parts linoleic diethanol amide and 5.5 parts of a pearlising agent. Similar results were also observed when the polysiloxanes were used in a conditioner with which the washed hair was rinsed and which comprised 0.75 parts of the polysiloxane and waxy fatty alcohols. When hair was treated with shampoo or conditioner containing the Example polysiloxane 3 and also a quaternary ammonium salt, for example Dehyquart CDB, the static present in the treated hair was substantially reduced.

That which is claimed is:

1. A method of treating fibrous material which comprises applying to the fibrous material a composition comprising a
polydiorganosiloxane having a group $=NCO(CHR-)_nOH$ connected with a silicon atom of a siloxane unit of the polydiorganosiloxane wherein R represents a hydrogen atom, a hydroxyl group, or a hydrocarbon group or a hydroxyl substituted hydrocarbon group and n has a value in the range 2 to 7.

2. A method according to claim 1 wherein the group $=NCO(CHR)_nOH$ is part of a substituent $-R''NXR'$ linked to the silicon atom wherein R" represents a divalent hydrocarbon group which may have a nitrogen, oxygen or sulphur atom present in the carbon chain, R' represents a hydrogen atom, a group X, an alkyl group having 1 to 20 carbon atoms, an alkenyl group or an aryl group, and X represents a group $-CO(CHR)_nOH$ wherein n has a value in the range 2 to 7.

3. A method according to claim 1 wherein n has the value 3, 4, 5 or 6.

4. A method according to claim 1 wherein each R represents a hydrogen atom.

5. A method according to claim 2 wherein the group R"NXR' is according to the formula R"NR'R'''NXR' wherein each R' is a hydrogen atom, each R" is a group $-(CH_2)_3-$, $-(CH_2)_4-$, or $-CH_2CH(CH_3)CH_2-$ and each R''' is a group $-(CH_2)_2-$.

6. A method according to claim 2 wherein the polydiorganosiloxane comprises at least one unit according to the general formula

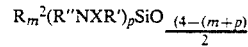

wherein $R^2$ represents a hydrogen atom or a hydrocarbon group having up to 8 carbon atoms, m has the value 0, 1 or 2 and p has the value 1 or 2, any remaining units being according to the general formula $$R_q^1 SiO_{\frac{4-q}{2}},$$

wherein $R^1$ represents a monovalent hydrocarbon group having up to 8 carbon atoms, and p has the value 0, 1, 2 or 3.

7. A method according to claim 6 wherein at least 80% of the groups $R^2$ and $R^1$ are methyl groups.

8. A method according to claim 1 wherein the polydiorganosiloxane has the general formula $(CH_3)_3SiO((CH_3)_2SiO)_x(CH_3Q'SiO)_zSi(CH_3)_3$ wherein the proportion of z to x is less than 0.5 to 1, and Q' represents $CH_2CH(CH_3)CH_2NHCH_2CH_2NHCO(CHR)_nOH$.

9. A method according to claim 1 wherein the composition is applied to the fibrous material in the form of an aqueous emulsion.

10. A method according to claim 1 wherein the fibrous material is a cotton fabric.

11. A fibrous material when treated by a method according to claim 1.

12. A method of treating fibrous material which comprises applying to the fibrous material a composition comprising a polysiloxane having one or more siloxane units according to the general formula (i)

$$R_m^2(R''NXR')_p SiO_{\frac{(4-(m+p))}{2}}$$

any remaining units of the polysiloxane being at least predominantly according to the general formula (ii)

$$R_q^2(R''NR^4H)_r SiO_{\frac{(4-(q+r))}{2}}$$

wherein $R^2$ represents a hydroxyl group, a group $R^1$, a group $OR^1$ or a group $COR^1$, $R^1$ represents a monovalent hydrocarbon group having up to 8 carbon atoms, $R^4$ represents a hydrogen atom, an alkyl group having 1 to 20 carbon atoms, an alkenyl group or an aryl group, R' represents a group $R^4$ or a group X, R'' represents a divalent hydrocarbon group which may have a nitrogen, oxygen or sulphur atom present in the carbon chain, X represents a group $CO(CHR)_nOH$ in which R represents a hydrogen atom, a hydroxyl group, a hydrocarbon group or a hydroxyl substituted hydrocarbon group, m has the value 0, 1 or 2, p has the value 1 or 2, q has the value 0, 1, 2 or 3, r has the value 0, 1 or 2 and n has a value in the range 2 to 7.

13. A method according to claim 12 wherein 95% or more of the siloxane units of the polysiloxane are according to the formula $$R_q^2 SiO_{\frac{(4-q)}{2}}$$

14. A method according to claim 12 wherein the polysiloxane is of the average general formula

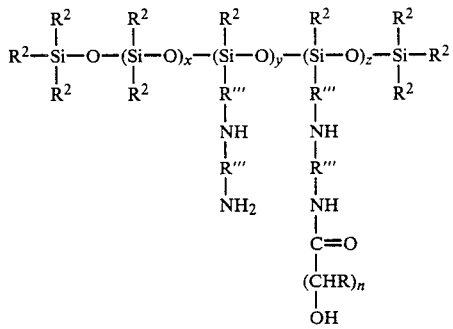

wherein not less than 80% of the groups $R^2$ are methyl groups, x has an average value from 20 to 1500, y has an average value from 0 to 50 and z has an average value from 0.5 to 50.

15. A method according to claim 14 wherein the ratio of y:z lies in the range 1:4 to 4:1.

16. A method according to claim 14 wherein the ratio x is less than 5:100.

17. A method according to claim 12 wherein the fibrous material is a cotton fabric and the composition is applied thereto in the form of an aqueous emulsion.

18. A method of treating fibrous material which comprises applying to the fibrous material a composition comprising a silane or a polysiloxane formed by hydrolysis or condensation of a silane, the silane being according to the general formula $R^1{}_zA_bSi(R''NXR')_c$ wherein A represents a hydroxyl or a hydrolysable group, $R^1$ represents a monovalent hydrocarbon group having up to 8 carbon atoms, R' represents a hydrogen atom, an alkyl group having 1 to 20 carbon atoms, an alkenyl group, an aryl group or a group X, R'' represents a divalent hydrocarbon group which may have a nitrogen, oxygen or sulphur atom present in the carbon chain, X represents a group $CO(CHR)_nOH$ in which R represents a hydrogen atom, a hydroxyl group, a hydrocarbon group or a hydroxyl substituted hydrocarbon group a has the value 0, 1 or 2, b has the value 1, 2 or 3, c has the value 1 or 2, the sum of $a+b+c=4$ and n has a value in the range 2 to 7.

19. A method according to claim 18 wherein the hydrolysable group A is a methoxy group and b has the value 2 or 3.

20. A method according to claim 18 wherein each R represents a hydrogen atom.

21. A method according to claim 18 wherein the group R''NXR' is according to the formula R''NR'R'''NXR' wherein each R' is a hydrogen atom, each R'' is a group $-(CH_2)_3-$, $-(CH_2)_4-$ or $-CH_2CH(CH_3)CH_2$ and each R''' is a group $-(CH_2)_2-$.

22. A method according to claim 18 wherein the group $R^1$ is methyl.

23. A method according to claim 18 wherein the fibrous material is a woven cotton fabric and the composition is applied thereto in the form of an aqueous emulsion.

* * * * *